(12) United States Patent
Arneth et al.

(10) Patent No.: US 6,841,999 B2
(45) Date of Patent: Jan. 11, 2005

(54) MAGNETIC RESONANCE IMAGING APPARATUS AND METHOD WITH ADHERENCE TO SAR LIMITS

(75) Inventors: Friedrich Arneth, Forchheim (DE); Gerhard Brinker, Erlangen (DE); Richard Koellner, Weisendorf (DE); Klaus Ludwig, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/269,687

(22) Filed: Oct. 11, 2002

(65) Prior Publication Data

US 2003/0098687 A1 May 29, 2003

(30) Foreign Application Priority Data

Oct. 11, 2001 (DE) .......................................... 101 50 137

(51) Int. Cl.⁷ ................................................. G01V 3/00
(52) U.S. Cl. ....................................... 324/309; 324/307
(58) Field of Search ................................ 324/300, 307, 324/309, 318, 314, 312

(56) References Cited

U.S. PATENT DOCUMENTS

| | | | |
|---|---|---|---|
| 5,144,238 A | | 9/1992 | Ehnholm |
| 5,492,122 A | * | 2/1996 | Button et al. ................ 600/411 |
| 6,115,489 A | | 9/2000 | Gupta et al. |
| 6,426,623 B1 | * | 7/2002 | Bernstein ..................... 324/314 |
| 2003/0080738 A1 | * | 5/2003 | Brinker et al. ............... 324/309 |
| 2003/0098688 A1 | * | 5/2003 | Brinker et al. ............... 324/309 |

FOREIGN PATENT DOCUMENTS

| | | | |
|---|---|---|---|
| JP | 3-284241 | * | 12/1991 |
| JP | 05-317287 | * | 12/1993 |
| JP | 07-222725 | * | 8/1995 |
| JP | 08-038447 | * | 2/1996 |
| JP | 11-253416 | * | 9/1999 |

OTHER PUBLICATIONS

Dina Simunic et al., "Spatial Distribution of High–Frequency Electromagnetic Energy in Human Head During MRI: Numerical Resuls and Measurements", IEEE, vol. 43, No. 1 Jan. 1996, pp. 88–94.*
Ji Chen et al., "Numerical Simulation of SAR and B1–Field Inhomogeneity of Shield RF Coils Loaded with the Human Head", IEEE, vol. 45, No. 5, May 1998, pp. 650–659.*

\* cited by examiner

*Primary Examiner*—Diego Gutierrez
*Assistant Examiner*—Dixomara Vargas
(74) *Attorney, Agent, or Firm*—Schiff Hardin LLP

(57) ABSTRACT

In a method and apparatus for magnetic resonance imaging with adherence to SAR limit values, a patient is subjected to a radio-frequency pulse sequence via at least one transmission antenna and the magnetic resonance signals that are produced are acquired in a spatially resolved manner via at least one reception antenna and are further-processed for producing magnetic resonance images or spectra, with current SAR values, determined before the implementation of the measurement on the basis of patient data and the position of the patient relative to the transmission antenna for planned parameters of the measurement, being modified as warranted until the current SAR values lie within the SAR limit values. The determination of the current SAR values ensues by comparing the current measurement situation to pre-defined measurement situations stored in a data bank for which pre-calculated SAR values are stored. The stored SAR value of the measurement situation of the data bank coming closest to the current measurement situation is utilized as the current SAR value. A reduction of the calculating outlay for determining the SAR values during the examination is achieved, and the data bank values can be calculated highly detailed, allowing a more exact determination of the current SAR values. The reduction of the safety margins that is achieved allows an enhancement of the system performance for the user, so that the user can implement the measurements in a shorter time and/or simultaneously acquire a number of tomograms.

14 Claims, 2 Drawing Sheets

MAGNETIC RESONANCE IMAGING APPARATUS AND METHOD WITH ADHERENCE TO SAR LIMITS

BACKGROUND OF THE INVENTION

1. Field of the Invention

The present invention is directed to a method for magnetic resonance imaging with adherence to SAR$^s$(Specific Absorption Rate) limit values of the type, wherein a patient is subjected to a radio-frequency pulse sequence via at least one transmission antenna for the implementation of a measurement in a magnetic resonance tomography apparatus, and magnetic resonance signals that are produced are acquired in a spatially resolved manner via at least one reception antenna and further-processed for producing magnetic resonance images or spectra, with current SAR values being determined before the implementation of the measurement on the basis of patient data and the position of the patient relative to the transmission antenna for planned parameters of the measurement, and wherein the parameters are modified as warranted until the current SAR values lie within the SAR limit values. The invention also is directed to a magnetic resonance system for the implementation of such a method.

2. Description of the Prior Art

Magnetic resonance tomography is a known technique for acquiring images of the inside of the body of an examination subject. For implementation of magnetic resonance tomography, a basic field magnet generates a static, relatively homogeneous basic magnetic field. Rapidly switched gradient fields for location coding that are generated by, gradient coils, are superimposed on this basic magnetic field during the exposure of magnetic resonance images. Sequences of radio-frequency pulses for triggering magnetic resonance signals are emitted into the examination subject with one or more radio-frequency transmission antennas. The magnetic resonance signals produced as a result of these radio-frequency pulses are received by radio-frequency reception antennas. Tomograms of the inside of the body of the patient are calculated and displayed on the basis of the magnetic resonance signals received from the field of view (FoV) under observation, possibly covering one or more body slices of the patient.

All body regions from the head to the foot can be measured in this way by displacement of the patient bed within the magnetic resonance tomography apparatus.

An important requirement in modern magnetic resonance tomography is the capability for fast imaging. This demand results from economic considerations of being able to examine as many patients as possible within a given time interval and, as well as from specific medical questions wherein a fast imaging is required for the examination result. One example of this is the reduction of motion artifacts due to movement of the patient during the measurement.

The high repetition rate of the radio-frequency transmission pulses and transmission pulse sequences required for a fast imaging, however, leads to a higher stress on the patient from electromagnetic radiation. Due to legal regulations, limit values are prescribed for this SAR (SAR=Specific Absorption Rate) stress that cannot be exceeded in magnetic resonance imaging. Since modern magnetic resonance tomography systems are technically capable of stressing patients with significantly higher SAR values, arrangements referred to as SAR monitors must be utilized in order to assure adherence to the limit values in the measurement. In addition to whole-body SAR values, specific limit values also must be adhered to for various body regions, and a fundamental distinction must be made between whole-body, partial body and local exposures.

The SAR stress is dependent on the individual patient data as well as on the position of the patient relative to the transmission antenna, the type of transmission antenna, and the transmission power (which is essentially defined by the type of pulse sequence) the flip angle of the RF pulses employed, the repetition rate, and the number of simultaneously acquired slices. The parameters of the measurement are usually summarized in a measurement protocol.

German OS 40 42 212 discloses a method for magnetic resonance imaging wherein the magnetic primary field is cyclically switched between two field strengths during the implementation of a measurement in order to adhere to the SAR limit values. Further details about the determination of the SAR values are not provided in this publication.

The determination of the SAR values for a particular measurement situation, i.e. for the individual data of the patient, the position of the patient relative to the transmission antenna, the type of transmission antenna or antennas, the radio-frequency pulse power as well as the further measurement parameters such as repetition rate or number of slices to be measured, conventionally has ensued at the beginning of the actual measurement. Due to the numerous influencing parameters, a very rough simulation model is utilized for the calculation of the current SAR values in order to keep the time expenditure for the calculation within limits. The application of a very rough simulation model, however, requires that correspondingly large tolerances be taken into consideration.

German OS 198 29 640 discloses a method for the implementation of an image-based diagnosis with which the cause or alleviating measures for artifacts that occur in the images of an imaging facility such as, for example, an MR tomography apparatus are identified. In this method, historic artifact images of a number of imaging facilities together with the measures for eliminating the respective artifacts are maintained in a data bank. Suitable measures for the elimination of the artifacts can be derived by comparing the artifacts under examination to the historic data. This publication, however, contains no discussion relating to measures for determining the SAR values.

SUMMARY OF THE INVENTION

An object of the present invention is to provide a method as well as an apparatus form magnetic resonance imaging with adherence to SAR values wherein a more precise determination of the SAR values is enabled, with a reduced time expenditure and, in particular, lower tolerances for the determination of these values immediately before the implementation of the measurement as well as during the pre-planning of a number of measurements in succession—even with intervening displacement of the patient bed.

This object is achieved in the method and the apparatus of the invention wherein the determination of the current SAR values ensues by comparing the current measurement situation to pre-defined measurement situations stored in a data bank for which respective pre-calculated SAR values are stored. The stored SAR value of the measurement situation of the data bank coming closest to the current measurement situation is utilized as current SAR value. Given deviating patient data and/or deviating parameters of the measurement, the stored SAR value is scaled according to the deviations. A "measurement situation" is the totality of known data relating to the measurement to be implemented that are relevant for the calculation of the SAR values. These data can include patient data such as weight, size, body type and the composition of the tissue of the patient, the position of the patient relative to the transmission antenna during the measurement, the type and geometry of the transmission antenna, as well as the parameters of the measurement itself such as, for example, the number of slices to be measured, the body regions to be examined, the type of pulse sequence, the repetition rate, as well as the RF pulse power, all of which are summarized in a measurement protocol.

In a known way, the current SAR values are differentiated and separately determined according to the designations "whole body", "partial body" and "local" as well as, partly, according to body regions (for example, partial body head, locally in the head, locally in the extremities, eyes, reproductive organs, etc.). Of course, they must thereby lie within the appertaining limit values.

The measurement situations stored in the data bank may exactly coincide with the current measurement situation, so that no scaling whatsoever of the stored SAR values is required. When the data of the closest measurement situation do not agree with the current measurement situation, then the stored SAR values are scaled in relationship to the deviation of the respective deviating quantity.

The data of the data bank can be very exactly calculated in advance since the necessary calculations can be produced off-line and the available calculating time is therefore not a fundamental concern—in contrast to online calculation during the examination. Once calculated, the result can be employed arbitrarily often. The data ban preferably contains SAR values for a number of measurement situations, particularly for whole-body measurement, partial body measurement or local measurement, for various patient groups from infant to adult—differentiated from svelte to fat, muscular to adipose—, for different bed positions from head to foot, for different coils or antenna systems such as, for example, whole-body antenna, body resonator or transmitting head coil. The stored SAR values are calculated for each measurement situation, preferably based on a reference condition that advantageously allows the simple scaling of the data bank SAR values to the measurement situation established by the current protocol parameters. The reference condition can be referred to a meaningful transmission power, for example 1 W, or to the power of a reference pulse. Alternatively, the reference can be to a reference field strength, for example the B1 field strength (i.e. the magnetic component of the RF field) occurring during a reference pulse or to some other field strength (for example, 1 $\mu$T).

Given utilization of volume coils that generate a relatively uniform B1 field in the patient, it is thus possible to fix the reference condition to a reference B1 field strength. Given such coils, the transmission power usually is set by means of a patient-dependent adjustment measurement that the flip angles of the RF pulses specified for the measurement or sequence protocols are exactly achieved. The flip angle is strictly linear relative to the applied B1 field strength. The time average of the B1 field strength of each measurement protocol can be unambiguously calculated, or preferably is already indicated as a parameter of the measurement protocol. The calculated SAR values normalized to the reference B1 field strength for the respective measurement situation then only have to be scaled with the average B1 field strength of the protocol, and it must be recognized that the B1 field strength enters approximately quadratically into the SAR values given currently utilized frequencies of the MR systems. A modified dependency must be employed in the scaling at other frequencies.

Given utilization of non-volume coils, it is advantageous to fix the reference condition to a normalized transmission power, for example 1 W. Given utilization of a protocol with a transmission power of 100 W, for example, the data bank values merely have to be multiplied by a factor of 100 for scaling.

The inventive method offers the advantage of a minimal calculating outlay for determining the current SAR values during an examination. For determining these values, the most applicable case merely must be found in the data bank and be scaled with the pulse data of the parameters employed or the protocol employed, in order to thus obtain the current SAR values. This time expenditure for the comparison and, if necessary, a simple scaling, is minimal. The enhanced dependability of the values allows the employment of comparatively small safety margins in the final determination of the current SAR values. This means an improvement in the performance for the user because either the measurement times can be shortened and/or more tomograms can be simultaneously acquired. Another significant advantage of the present invention is that arbitrarily detailed models for the SAR calculation can be utilized for the calculation of the measurement situations pre-defined in the data bank. The calculating time required therefor need be expended only once since the calculations are implemented independently thereof off-line. By allowing the use of a correspondingly more detailed data bank, the present method thus enables a more precise and faster determination of the SAR values that exist in the current measurement.

The calculation of the SAR values stored in the data bank can ensue, for example, by means of the finite elements method or comparable methods.

DESCRIPTION OF THE PREFERRED EMBODIMENTS

Figure 1:
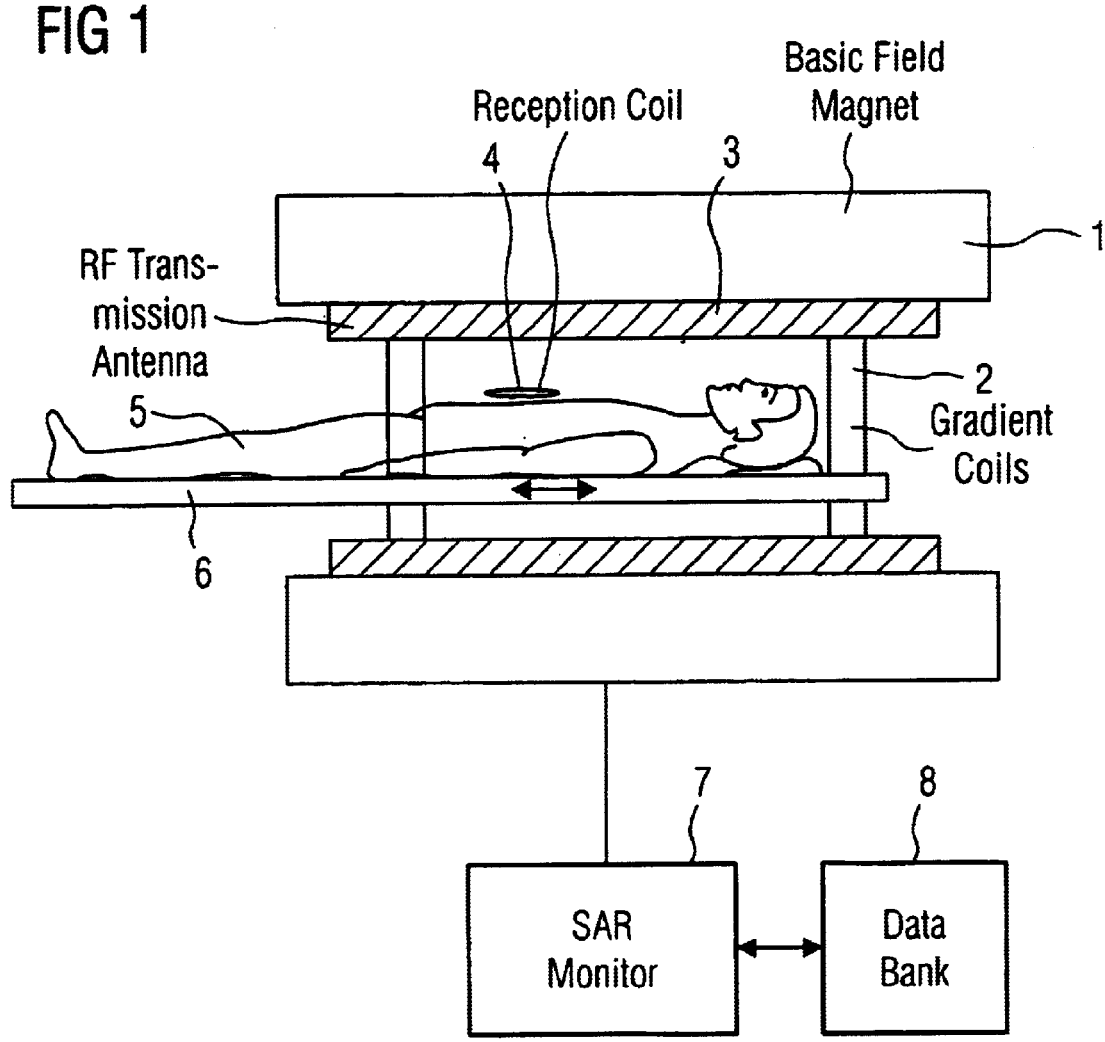
FIG. 1 is a block diagram as an example of the basic components of a magnetic resonance tomography apparatus with which the present method can be implemented.

FIG. 1 schematically shows a cross-section through a magnetic resonance tomography apparatus. FIG. 1 shows only the basic components of the apparatus, a basic field magnet 1, a gradient coil system 2, a radio-frequency transmission antenna 3 as well as a reception coil 4. This can be a pure reception coil optimized for the specific diagnostic inquiry or a local coil as frequently utilized, for example, in spectroscopic applications. Further, a patient 5 is shown on a patient bed 6 that is movable within the magnetic resonance tomography apparatus in the direction indicated with the arrow. In the measurement, radio-frequency pulses for generating magnetic resonance signals are emitted into the body of the patient 5 via the radio-frequency transmission antenna 3 fashioned as whole-body coil. The resulting magnetic resonance signals are acquired with the reception coil 4 or with the radio-frequency antenna 3, which can also be operated as receiver, and are presented in the form of a two-dimensional magnetic resonance image of the respectively covered measurement region. Of course, other, specific reception antennas can be utilized for the acquisition of the magnetic resonance signals. For covering body regions lying outside the measurement region, these body regions are moved into the center of the magnet with the patient bed 6, so the position of the patient relative to the transmission antenna 3 changes.

FIG. 1 also shows a unit 7 for the calculation of the SAR values, referred to as an SAR monitor, that has access to a data bank 8. SAR values for a multitude of different measurement situations are stored in the data bank 8.

Figure 2:
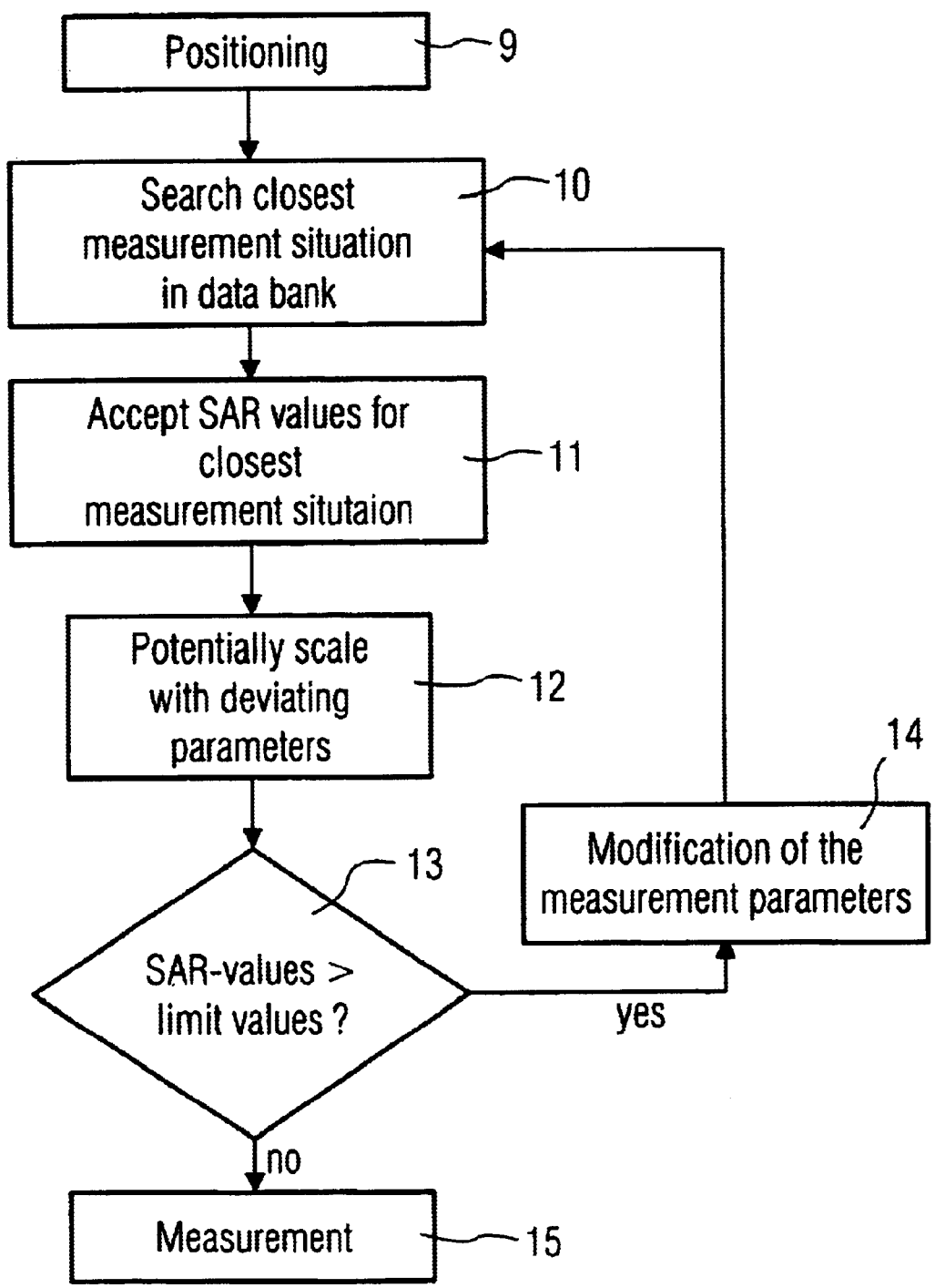
FIG. 2 is a flowchart for the implementation of the inventive method in an exemplary embodiment.

In an exemplary embodiment, FIG. 2 shows a flowchart for the implementation of the present method. The patient 5 is first positioned on the patient bed 6 according to the intended measurement (step 9). Subsequently, a measurement situation coming closest to the present measurement situation is sought in the data bank 8 by means of a suitable search for this specific measurement situation established by the patient 5, the bed 6 and the transmission coil 3 (step 10). The measurement situation thereby contains the type of transmission coil employed, the patient data, the bed position of the patient 5 as well as the planned measurement parameters. After the identification of the closest measurement situation in the data bank 8, the SAR values stored for this measurement situation are reviewed (step 11). Given a deviation from the measurement situation found in the data bank 8 from the current measurement situation, the stored SAR values are scaled according to the size of the deviation in order to obtain the current SAR values (step 12).

A comparison to the SAR limit values is carried out after this determination of the current SAR values for the planned measurement parameters in order, given upward transgression of the limit values, to again be able to modify the parameters for adherence to the limit values (steps 13, 14). When the current SAR values adhere to the SAR limit values, then the actual measurement 15 can ensue.

The determination of relatively exact SAR values is enabled in this way. The tolerance to be taken into consideration for safety reasons are correspondingly smaller. This in turn denotes an enhancement of the system performance in the respect that the measurement time can be shortened and/or a larger number of tomograms can be simultaneously acquired.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for magnetic resonance imaging with adherence to specific absorption rate (SAR) limit values, comprising the steps of:
    subjecting a patient, having patient data associated therewith, to a magnetic resonance measurement, having planned parameters associated therewith, by exposing said patient to a radio-frequency pulse sequence using at least one transmission antenna and thereby exciting magnetic resonance signals in said patient, and acquiring said magnetic resonance signals in a spatially resolved manner via at least one reception antenna, and processing said magnetic resonance signals to obtain an examination result selected from the group consisting of a magnetic resonance image and a spectrum;
    storing a plurality of calculated SAR values in a databank respectively for a plurality of different predefined measurement situations, said different measurement situations being respectively dependent at least on different patient data and different planned parameters;
    identifying a current measurement situation for said magnetic resonance measurement, before conducting said magnetic resonance measurement and comparing said current measurement situation to said predefined measurement situations stored in said databank to identify a calculated SAR value for a predefined measurement situation stored in said databank which most closely resembles said current measurement situation, and initially setting a current SAR value to be equal to the identified calculated SAR value; and
    modifying said planned parameters as needed until said current SAR value is within a predetermined SAR limit value.

2. A method as claimed in claim 1 comprising the additional step of, before modifying said planned parameters as needed, scaling said current SAR value as needed dependent on deviations, if present, between said current measurement situation and the pre-defined measurement situation in said databank most closely resembling said current measurement situation.

3. A method as claimed in claim 1 wherein said plurality of calculated SAR values are each referenced to a reference condition for different patient data, different body regions, different transmission antennas, and different positions of a patient relative to the transmission antenna in said plurality of predefined measurement situations.

4. A method as claimed in claim 1 comprising calculating said plurality of calculated SAR values based on respective simulation models for said plurality of predefined measurement situations.

5. A method as claimed in claim 1 comprising employing parameters selected from the group consisting of repetition rate of said radio-frequency pulse sequence, plurality of slices of said patient from which said magnetic resonance signals are obtained, slice thickness of a slice of said patient from which said magnetic resonance signals are obtained, a flip angle of pulses in said radio-frequency pulse sequence, as said planned parameters which are modified until said current SAR value is within said SAR limit value.

6. A method as claimed in claim 1 wherein said planned parameters include a measurement time of said magnetic resonance measurement, and wherein the step of modifying at least one of said planned parameters comprises lengthening said measurement time until said current SAR value is within said SAR limit value.

7. A method as claimed in claim 1 comprising automatically comparing said current measurement situation to said plurality of predefined measurement situations in said databank after specifying said patient data and selecting a measurement protocol containing said planned parameters.

8. A magnetic resonance system for magnetic resonance imaging with adherence to specific absorption rate (SAR) limit values, comprising:
    an examination unit adapted to receive subjecting a patient, having patient data associated therewith, for conducting a magnetic resonance measurement, having planned parameters associated therewith, by exposing said patient to a radio-frequency pulse sequence using at least one transmission antenna and thereby exciting magnetic resonance signals in said patient, and acquiring said magnetic resonance signals in a spatially resolved manner via at least one reception antenna, and processing said magnetic resonance signals to obtain an examination result selected from the group consisting of a magnetic resonance image and a spectrum;
    a databank containing stored plurality of calculated SAR values in a databank respectively for a plurality of different predefined measurement situations, said different measurement situations being respectively dependent on different patient data and different planned parameters;
    an SAR monitor having access to said databank for identifying a current measurement situation for said magnetic resonance measurement before conducting said magnetic resonance measurement and for comparing said current measurement situation to said pre-defined measurement situations stored in said databank to identify a calculated SAR value for a predefined measurement situation stored in said databank which most closely resembles said current measurement situation, and initially setting a current SAR value to be equal to the identified calculated SAR value; and an input unit allowing modification of modifying said planned parameters as needed until said current SAR value is within a predetermined SAR limit value.

9. A magnetic resonance system as claimed in claim 8 comprising wherein said SAR monitor, before modifying said planned parameters as needed, scales said current SAR value as needed dependent on deviations, if present, between said current measurement situation and the pre-defined measurement situation in said databank most closely resembling said current measurement situation.

10. A magnetic resonance system as claimed in claim 8 wherein said plurality stored of calculated SAR values are each referenced to a reference condition for different patient data, different body regions, different transmission antennas, and different positions of a patient relative to the transmission antenna in said plurality of predefined measurement situations.

11. A magnetic resonance system as claimed in claim 8 wherein said stored plurality of calculated SAR values are calculated based on respective simulation models for said plurality of predefined measurement situations.

12. A magnetic resonance system as claimed in claim 8 wherein said input unit allows modification of employing parameters selected from the group consisting of repetition rate of said radio-frequency pulse sequence, plurality of slices of said patient from which said magnetic resonance signals are obtained, slice thickness of a slice of said patient from which said magnetic resonance signals are obtained, a flip angle of pulses in said radio-frequency pulse sequence, as said planned parameters which are modified until said current SAR value is within said SAR limit value.

13. A magnetic resonance system as claimed in claim 8 wherein said planned parameters include a measurement time of said magnetic resonance measurement, and wherein said input unit allows lengthening of said measurement time until said current SAR value is within said SAR limit value.

14. A magnetic resonance system as claimed in claim 8 wherein said SAR monitor automatically compares said current measurement situation to said plurality of predefined measurement situations in said databank after specifying said patient data are specified and a measurement protocol containing said planned parameters is selected via said input unit.

* * * * *